(12) United States Patent
Imran

(10) Patent No.: US 10,137,280 B2
(45) Date of Patent: Nov. 27, 2018

(54) SYSTEM AND METHOD FOR TREATMENT OF HEMORRHAGIC STROKE

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 682 days.

(21) Appl. No.: 13/529,608

(22) Filed: Jun. 21, 2012

(65) Prior Publication Data
US 2013/0158510 A1   Jun. 20, 2013

Related U.S. Application Data

(60) Provisional application No. 61/503,439, filed on Jun. 30, 2011.

(51) Int. Cl.
| | |
|---|---|
| *A61K 45/06* | (2006.01) |
| *A61M 25/10* | (2013.01) |
| *A61K 38/18* | (2006.01) |
| *A61M 25/00* | (2006.01) |
| *A61B 17/12* | (2006.01) |
| *A61K 9/00* | (2006.01) |

(52) U.S. Cl.
CPC ......... *A61M 25/10* (2013.01); *A61B 17/1214* (2013.01); *A61B 17/12031* (2013.01); *A61B 17/12113* (2013.01); *A61B 17/12186* (2013.01); *A61K 38/185* (2013.01); *A61K 38/1841* (2013.01); *A61K 45/06* (2013.01); *A61M 25/0043* (2013.01); *A61K 9/0024* (2013.01); *A61M 2025/0042* (2013.01)

(58) Field of Classification Search
None
See application file for complete search history.

(56) References Cited

U.S. PATENT DOCUMENTS

| | | | |
|---|---|---|---|
| 4,655,746 | A | 4/1987 | Daniels et al. |
| 5,212,162 | A | 5/1993 | Missel et al. |
| 5,312,356 | A | 5/1994 | Engelson et al. |
| 5,690,667 | A | 11/1997 | Gia |
| 7,706,873 | B2 | 4/2010 | Ammirati |
| 7,820,202 | B2 | 10/2010 | Bodmeier |
| 2004/0156781 | A1 | 8/2004 | Porter et al. |
| 2004/0156904 | A1 | 8/2004 | Saltman et al. |
| 2005/0158272 | A1 | 7/2005 | Whirley et al. |
| 2005/0255091 | A1 * | 11/2005 | Loomis .................. 424/93.7 |
| 2006/0116713 | A1 | 6/2006 | Sepetka et al. |
| 2006/0193877 | A1 | 8/2006 | Tengler et al. |
| 2007/0100318 | A1 | 5/2007 | Seward et al. |
| 2009/0076540 | A1 | 3/2009 | Marks et al. |
| 2009/0175944 | A1 * | 7/2009 | Ringeisen .......... A61L 27/20 424/484 |
| 2009/0209658 | A1 | 8/2009 | Goupil et al. |
| 2009/0326508 | A1 * | 12/2009 | Braun et al. .................. 604/500 |
| 2010/0100106 | A1 | 4/2010 | Ferrera |

FOREIGN PATENT DOCUMENTS

WO   WO99/56783   * 11/1999   ............. A61K 47/30

OTHER PUBLICATIONS de Gast et al., Transforming Growth Factor beta-coated Platinum Coils for Endovascular Treatment of Aneurysms: An Animal Study. Neurosurgery, vol. 49, No. 3, Sep. 2001, 690-696.*
Kilic et al., Intravenous TAT-GDNF Is Protective After Focal Cerebral Ischemia in Mice. Stroke. 2003;34:1304-1310.*
Frosen et al., Growth Factor Receptor Expression and Remodeling of Saccular Cerebral Artery Aneurysm Walls: Implications for Biological Therapy Preventing Rupture. Neurosurgery vol. 58 | No. 3 | Mar. 2006, 534-541.*
Yagi et al., Rescue of ischemic brain injury by adenoviral gene transfer of glial cell line-derived neurotrophic factor after transient global ischemia in gerbils. Brain Research 885 (2000) 273-282.*
Lee et al., Human neural stem cells overexpressing glial cell line-derived neurotrophic factor in experimental cerebral hemorrhage. Gene Therapy (2009) 16, 1066-1076.*
Hoare et al., Hydrogels in drug delivery: Progress and challenges. Polymer 49 (2008) 1993-2007.*
Fiorella, et al. In-stent stenosis as a delayed complication of neuroform stent-supported coil embolization of an incidental carotid terminus aneurysm. AJNR Am J Neuroradiol. Nov.-Dec. 2004;25(10):1764-7.
International search report dated Dec. 7, 2012 for International Application No. PCT/US2012/044270.
Luzardo, et al. Balloon-assisted coiling through a single 6F guiding catheter. AJNR Am J Neuroradiol. Jan. 2006;27(1):190-1.
Honmou, et al. Intravenous adminsitration of auto serum-expanded autologous mesenchymal stem cells in stroke. Brain. Jun. 2011;134(Pt 6):1790-807. Epub Apr. 14, 2011.
Willinsky, et al. Use of a second microcatheter in the management of a perforation during endovascular treatment of a cerebral aneurysm. AJNR Am J Neuroradiol. Sep. 2000; 21:1537-1539.
Kilic, et al. Intravenous TAT-GDNF is protective after focal cerebral ischemia in mice. Stroke. May 2003;34(5):1304-10. Epub Apr. 3, 2003.

* cited by examiner

*Primary Examiner* — John D Ulm
(74) *Attorney, Agent, or Firm* — Wilson Sonsini Goodrich and Rosati, P.C.

(57) ABSTRACT

Embodiments of the invention provide apparatus, methods and systems for delivering treatments and for medications to the site of an aneurysm (SOA). One embodiment of a method comprises delivering a neural growth stimulating factor (NGSF) to the site of the aneurysm to grow new nerve cells and/or stimulate the regeneration of damaged nerve cells. The NGSF may be delivered in a carrier such as a gel which can be selected to allow for long term delivery of the NGSF to the SOA. In many embodiments, the NGSF may be delivered to the SOA using a micro-catheter based system which includes a microcatheter that can be advanced in the cerebral vasculature. The microcatheter may also be used to delivery occlusive element to the SOA such as occlusive coils or balloon which promote clotting and reduce bleeding at the SOA and together with the carrier allow for long term release of NGSF.

18 Claims, 2 Drawing Sheets

SYSTEM AND METHOD FOR TREATMENT OF HEMORRHAGIC STROKE

RELATED APPLICATIONS

This application claims the benefit of priority of Provisional U.S. Patent Application Ser. No. 61/503,439, entitled "System and Method for Treatment of Hemorrhagic Stroke" filed Jun. 30, 2011; which is fully incorporated by reference herein for all purposes.

BACKGROUND

Field of the Invention

Embodiments of the invention relate to drug delivery devices and methods of use thereof. More specifically, embodiments of the invention relate to drug delivery devices and methods for delivering neural growth and protective factors to the site of a cerebral aneurysm.

Strokes afflict millions of Americans each year and result in significant morbidity and mortality. During a stroke, one or more areas of the brain can be damaged. Depending upon the area affected, a person may lose the ability to move one side of the body, the ability to speak, or a number of other functions. The damage may be temporary or permanent, and the function may be partially or completely lost. A person's long term outcome depends upon how much brain is damaged, how quickly treatment begins, and a number of other factors.

Hemorrhagic stroke is one of the primary causes of stroke and is due to bleeding into brain tissue from the rupture or tear of the wall of an enlarged blood vessel in the brain known as a cerebral aneurysm. Current interventional radiological methods for treating the aneurysm prior to rupture rely on the placement of a coil or other occlusive device, such as a vascular clip, at the site of the aneurysm to form a clot in the aneurysm and reduce the risk of rupture. Such methods, however, have limited use after rupture for treating local brain tissue that has been affected by ischemia and hypoxia resulting from the hemorrhage. Such effects can result in neural cell death at the ischemic site in turn causing loss of brain function at the affected cite.

What is needed therefore is a treatment for reducing the effects which follow hemorrhagic stroke, such as inflammation, as well as for stimulating nerve re-growth at the affected site to grow new nerve cells and/or stimulate the regeneration of damaged nerve cells.

SUMMARY OF THE INVENTION

Various embodiments of the invention provide apparatus, methods and systems for delivering treatments and medications to the site of an aneurysm. The delivery may be prior to rupture but more often will be following a partial or total rupture to prophylactically treat or ameliorate the effects of hemorrhagic stroke and to stimulate the repair of damaged nerve tissue, and new nerve tissue at the site. Many embodiments of the invention provide a catheter-based system including a delivery catheter and therapeutic composition to be delivered to the site. The composition can comprise a gel or other drug carrier and one or more therapeutic agents such as neural growth stimulating agents, neural protective agents, anti-inflammatory agents, and calcium channel modulators.

In particular embodiments, the composition may comprise a transforming growth factor-β, such as glial cell derived neurotrophic factor (GDNF), a potent neurotrophic factor that promotes the survival of neurons. The gel or other carrier may also be saturated with oxygen to deliver oxygen to the affected ischemic site. In many embodiments the gel comprises a thixotropic material which is gel like under normal conditions, but has liquid like properties when shaken, agitated, or otherwise subjected to shear stress e.g. when being extruded through a delivery lumen. Such materials allow the gel to be delivered by means of a cerebral catheter to the target tissue cite in the brain and then become a gel again at the site so as to provide for localized drug delivery of the therapeutic agents to tissue at the affected site. The gel in essence functions as a drug depot or reservoir allowing for extended delivery of the therapeutic agents at the site.

The specific rheological properties of the gel (e.g., static and dynamic viscosity) can be selected to control the rate of release of one or more therapeutic agents from the gel. Higher viscosity gels can be selected for slower rates of release and versa visa. In specific embodiments, the gel can comprise a first and second gel component having a faster and slower rate of release due to differences in viscosity or other property of each component. In use, such embodiments allow for both an immediate and longer term release of one or more therapeutic agents from the gel, In particular embodiments, the faster release gel can include a first group of therapeutic agents to be immediately released to treat the acute symptoms of stroke, (e.g., inflammation, hypoxia, etc); and the slower release gel can include a second group of agents to be released over a longer term to treat the long term consequences of stroke (e.g., nerve cell damage t and death). The first group can include anti-inflammatory, neuro-protective and calcium channel modulators agents while the second group can include nerve cell growth stimulating agents. In related embodiments, the gel can be configured to release one or more therapeutic agents in response to conditions resulting from stroke, e.g., hypoxia, pH change, increased cranial pressure, so as to immediately treat a stroke as it happens or quickly thereafterwards. In one embodiment, this can be achieved again through the use of thixotropic materials which undergo a reduction in viscosity in response to the flow of blood from the site of the hemorrhage. In specific embodiments, such agents can include a coagulant to cause rapid coagulation at the site of the hemorrhage. In some embodiments, such gels can be positioned at the site of a cerebral aneurysm before the aneurysm ruptures (or after it is repaired) so as to provide a rapid localized delivery of one or more therapeutic agents to treat the affected tissue and even stop the hemorrhage soon after it occurs. For embodiments involving the delivery of embolization inducing coils or a vascular clip to treat the aneurysm, the gel can be positioned in the area between or near the coils or vascular clip.

In the first aspect of the present invention, methods for treating cerebral aneurysms comprise delivering a neural growth stimulating agent to the aneurysm. The neural growth stimulating agent typically comprises a member of the transforming growth factor-β family, usually comprising glial cell derived neurotrophic factor (GDNF). The neural growth stimulating factor will typically be present in a carrier suitable for delivery or infusion through a catheter to an aneurysmal site within the arterial cerebral vasculature. To facilitate delivery through the microcatheter, which will typically have a very small lumen, the carrier is preferably thixotropic where the viscosity of the fluid is reduced when subjected to the shear forces experienced during delivery through the small catheter lumen, thus, the thrixotropic carrier will allow a reduced pressure or force for delivery through the catheter while allowing the delivered composition to regain viscosity (with a reduced risk of loss from the deliver site) after the material is delivered to the aneurysm. Particularly suitable carriers comprise gels, preferably thixotropic gels.

In addition to the neural growth stimulating agent, the materials, compositions, or formulations that are delivered to the aneurysm may comprise a variety of additional active or inactive agents. For example, the fluid carrier may be saturated with oxygen to reverse the effects of hypoxia. Additionally, anti-inflammatory agents may be added to the carrier, such as dexamethasone so as to reduce or prevent inflammation at the aneurysm site. Other beneficial agents which may be added include neural protective agents, calcium channel blockers, and the like. While these supplementary agents will typically be combined with the neural growth stimulating agent in the carrier, the methods of the present invention would also extend to delivery of these agents in a sequential manner, where the supplemental agents may be delivered before, after, and/or simultaneously with the delivery of the neural growth stimulating agents.

The methods of the present invention may be used to treat cerebral aneurysms prophylactically, i.e., prior to any significant rupture of the aneurysm or blood loss into the brain tissue. The methods may find greater use, however, in treating the cerebral aneurysms after rupture has commenced or occurred. In both such cases, it will often be useful to combine the carrier with occlusive elements which mechanically promote clotting within the aneurysmal sac prior to or shortly after rupture of the sac. Such occlusive elements are well known in the art, typically comprising microcoils, microballoons, hydrateable fibers and materials, and other bulking agents which both fill volume within the aneurysm and promote clotting of blood.

In another aspect of the present invention, systems are provided for delivering a neural growth factor to a cerebral aneurysm. The systems comprise a microcatheter having a delivery lumen, where the microcatheter is adapted to be advanced to the site of the aneurysm in the cerebral vasculature. The systems will further include a source of neural growth factor suitable for delivery through the microcatheter to the aneurysm. Particularly preferred neural growth factors and other materials within the source of the neuronal growth factor are described above in connection with the methods of the present invention.

Further details of these and other embodiments and aspects of the invention are described more fully below, with reference to the attached drawing figures.

DETAILED DESCRIPTION OF THE INVENTION

The following terms and phrases are defined for use in the specification and in the appended claims.

Figure 1:
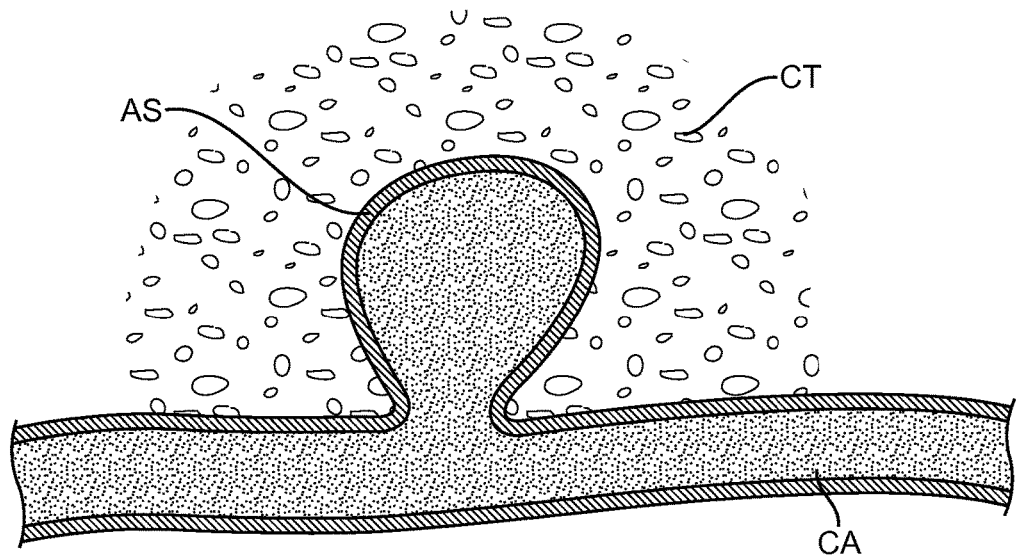
FIG. 1 illustrates the typical anatomy of an aneurysm in the cerebral vasculature.

The term "aneurysm" and phrase "cerebral aneurysm" are intended to have their common meanings as used in the medical and patent literature. In particular, aneurysms occur when there is an acquired or congenital weakness in the wall of an artery. Cerebral aneurysms occur in the cerebral arteries, and those which are most readily treated by the methods and systems of the present invention will generally be "saccular" where a portion of the wall expands or balloons outwardly into the cerebral tissue to form an aneurysmal sack AS, as illustrated in FIG. 1.

Figure 2:
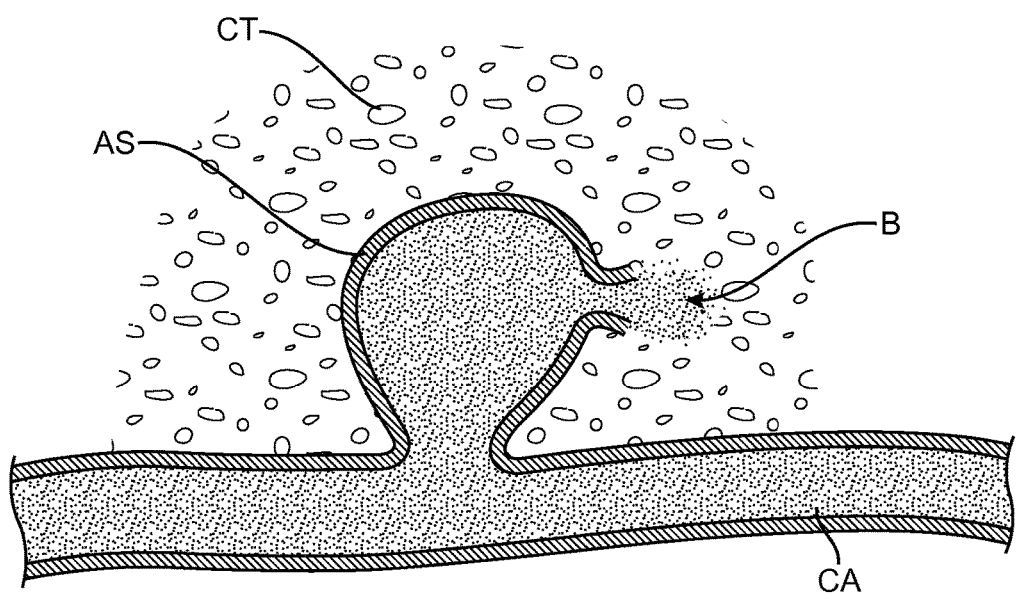
FIG. 2 illustrates the aneurysm of FIG. 1 as it begins to rupture.

Once the aneurysmal sack AS has formed, the risk of rupture greatly increases. As shown in FIG. 2, a portion of the weakened wall defining the aneurysmal sack may burst releasing blood B into the cerebral tissue CT.

The present invention relies on the delivery of neural growth factors to the aneurysm, typically to the aneurysmal sack in a cerebral aneurysm, to treat the aneurysm either before or after rupture. Suitable neural growth factors include growth factors which are members of the super family transforming growth factor-β, more particularly comprising glial cell derived neurotrophic factor (GDNF). Such growth factors are described and defined in KILIC (2003) Stroke 34:1304-1310, the full disclosure of which is incorporated herein by reference.

The neural growth factors will be delivered in a suitable pharmaceutical carrier, preferably a carrier displaying thixotropic properties by "thixotropic properties." It is meant the carrier will be thick and viscous under normal conditions, but will become less viscous when subjected to stress, particularly shear stresses involved in delivery through a very small lumen such as those found in microcatheters suitable for delivery of materials to the neurovasculature and in particular to aneurysms within the neurovasculature. Exemplary thixotropic delivery carriers and gels are described in U.S. Pat. No. 7,820,202; US 2006/0193877; U.S. Pat. No. 5,212,162; and elsewhere in the patent and medical literature. The full disclosures of these patents and patent publications are incorporated herein by reference.

In addition to the neural growth factors, the methods and compositions of the present invention may be used to deliver other active and inactive agents to the aneurysm or locations near the aneurysm. For example, anti-inflammatories may be delivered to the aneurysm. Suitable anti-inflammatory agents are listed, for example, in US 2007/0100318, the full disclosure of which is incorporated herein by reference.

Figure 3:
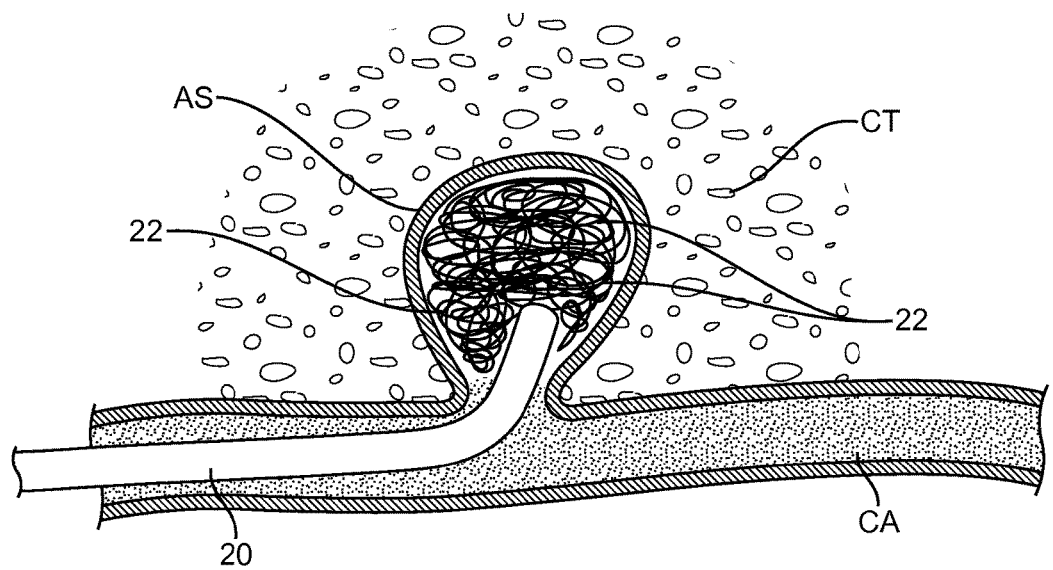
FIG. 3 illustrates delivery of the compositions of the present invention through a microcatheter in order to treat the rupturing aneurysm of FIG. 2.
Figure 4:
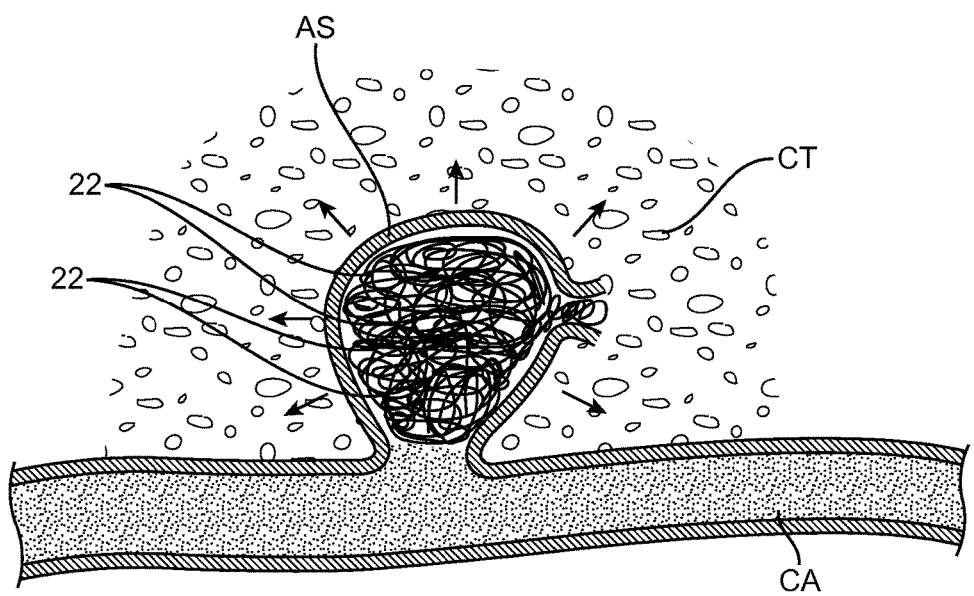
FIG. 4 illustrates the condition of the aneurysm after being treated in accordance with the principles of the present invention.

Referring now to FIGS. 3 and 4, in one or embodiments a microcatheter 20 may be used to deliver the therapeutic compositions of the present invention to the rupturing aneurysm shown in FIG. 2. The microcatheter is advanced to the aneurysmal sack AS through the cerebral artery CA in a conventional manner, typically under fluoroscopic guidance. The microcatheter 20 may be any one of a wide variety of cerebral microcatheters available commercially and/or described in the patent literature, for example, in U.S. Pat. Nos. 4,655,746; 5,312,356; 5,690,667; 7,706,873; and in published application US 2010/0100106, the full disclosures of which are incorporated herein by reference. Optionally, in addition to the compositions including the neural growth factor and other optional active agents as described above, the microcatheter may also be used to deliver occlusive elements, such as the microcoils 22 shown in FIGS. 3 and 4. Suitable microcoils are described in at least some of the patent references incorporated above and are also available commercially from a number of suppliers, such as Micrus Therapeutics. The coils and neural growth stimulating agent will fill or at least partially fill the aneurysmal sack AS and inhibit or stop bleeding. The neural growth stimulating agents will then promote regrowth of the nerves which may have been damaged by the ruptured aneurysm. The desired result is that the coils and fluid carrier with the neural growth stimulating agent, such as a thickened gel, will at least partially fill the aneurysmal sack AS and be able to release the neural growth stimulating agent over time into the surrounding brain tissue in order to promote healing of damaged nerve cells and generation of new nerve cells. In use, embodiments of such an approach serve to reduce the neurological damage associated with hemorrhagic stroke (e.g., loss of speech and/or motor function) and improve recovery and clinical outcomes.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be adapted depending upon the size and location of the aneurysm in the brain. They may also otherwise adapted for various pediatric applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for treating a cerebral aneurysm, the method comprising:
    advancing a microcatheter having a delivery lumen to the site of the aneurysm;
    delivering a carrier containing a first agent and a second agent to the aneurysm through the delivery lumen of the microcatheter so as to at least partially fill a sac of the aneurysm; wherein the first agent comprises an anti-inflammatory agent and the second agent comprises a member of the transforming growth factor-β family; and
    controllably releasing the first and second agents from the carrier to the site of the aneurysm,
    wherein the carrier comprises a first gel component including the first agent and a second gel component including the second agent,
    wherein the first gel component has a first viscosity selected to release the first agent at a first rate of release, and
    wherein the second gel component has a second viscosity different from the first viscosity, the second viscosity being selected to release the second agent at a second rate of release slower than the first rate of release.

2. A method as in claim 1, wherein the member of the transforming growth factor-β family comprises glial cell derived neurotrophic factor (GDNF).

3. A method as in claim 1, wherein the carrier displays thixotropic behavior when delivered to the aneurysm.

4. A method of claim as in claim 3, wherein the carrier also contains a coagulant, the carrier undergoing a reduction in viscosity in response to the flow of hemorrhaging blood at the aneurysm site so as to release the coagulant and stop or reduce the flow of blood from the hemorrhage at the aneurysm site.

5. A method as in claim 1, wherein the carrier is saturated with oxygen.

6. A method claim 1, further comprising delivering occlusive elements to the aneurysm.

7. A method as in claim 6, wherein the occlusive elements are delivered together with the first and second agents.

8. A method as in claim 6, wherein the occlusive elements comprise coils or balloons.

9. A method as in claim 6, wherein the occlusive elements promote clotting in the aneurysmal sac.

10. A method as in claim 6, wherein the occlusive elements result in at least partial filling of the aneurysmal sac.

11. A method as in claim 1, wherein the anti-inflammatory agent comprises dexamethasone.

12. A method for treating a cerebral aneurysm having an aneurysmal sac, the method comprising:
    advancing a microcatheter having a delivery lumen to a site of the aneurysm, the microcatheter delivery lumen configured to deliver both a gel carrier and occlusive elements to the aneurysm, wherein the gel carrier comprises a first gel component and a second gel component, the first gel component comprising a first agent and the second gel component comprising a second agent;
    delivering through the delivery lumen to the aneurysm site i) the gel carrier and ii) the occlusive elements;
    at least partially filling the aneurysmal sac with the gel and occlusive elements so as to have the gel and the occlusive elements stop or inhibit bleeding at the aneurysm site, wherein the first agent comprises an anti-inflammatory agent and the second agent comprises a member of the transforming growth factor-β family; and
    controllably releasing the first and second agents from the gel into the surrounding brain tissue so as to promote i) healing of injured nerve cells and/or ii) generation of new nerve cells in the surrounding brain tissue,
    wherein the first gel component has a first viscosity selected to release the first agent at a first rate of release, and
    wherein the second gel component has a second viscosity different from the first viscosity, the second viscosity being selected to release the second agent at a second rate of release slower than the first rate of release.

13. A method as in claim 12, wherein the occlusive elements comprise coils or balloons.

14. A method as in claim 12, wherein the occlusive elements promote clotting in the aneurysmal sac, the method further comprising:
    utilizing the occlusive elements to form a clot in the aneurysmal sac so as to stop or inhibit bleeding at the aneurysm site.

15. A method as in claim 12, wherein the member of the transforming growth factor-β family comprises glial cell derived neurotrophic agent (GDNF).

16. A method as in claim 12, wherein the carrier displays thixotropic behavior when delivered to the aneurysm site.

17. A method of claim as in claim 16, wherein the gel also contains a coagulant, the gel undergoing a reduction in viscosity in response to the flow of hemorrhaging blood at the aneurysm site so as to release the coagulant and stop or reduce the flow of blood from the hemorrhage at the aneurysm site.

18. A method as in claim 12, wherein the carrier is saturated with oxygen, the method further comprising:
    releasing oxygen from the carrier to reduce a degree of hypoxia in surrounding brain tissue.

* * * * *